US00PP36168P2

(12) United States Plant Patent
Hansen

(10) Patent No.: US PP36,168 P2
(45) Date of Patent: Sep. 24, 2024

(54) ***STOKESIA* PLANT NAMED 'Riptide'**

(50) Latin Name: ***Stokesia laevis* (Hill) Green**
Varietal Denomination: Riptide

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/445,632

(22) Filed: Nov. 29, 2023

(51) Int. Cl.
*A01H 5/02* (2018.01)
*A01H 6/14* (2018.01)

(52) U.S. Cl.
USPC ..... Plt./484

(58) Field of Classification Search
USPC ..... Plt./484
CPC ..... A01H 5/02; A01H 5/00; A01H 6/14
See application file for complete search history.

(56) References Cited

U.S. PATENT DOCUMENTS

PP23,090 P2 * 9/2012 van Heesbeen ..... A01H 6/14
Plt./484

* cited by examiner

*Primary Examiner* — June Hwu

(57) ABSTRACT

A new and distinct variety of *Stokesia laevis* plant named 'Riptide' with extended blooming of composite flowers having periwinkle-blue ray florets and purplish-blue disk florets just above the deep-green foliage of compact rounded plants from early summer until fall. The new plant is suitable for garden landscapes, in containers, or as a cut flower.

2 Drawing Sheets

Botanical classification: *Stokesia laevis* (Hill) Green.
Variety denomination: 'Riptide'.

STATEMENT REGARDING PRIOR DISCLOSURES UNDER 37 CFR 1.77(b)(6)

The sale or offer for sale of the new plant was made by Walters Gardens, Inc. on Dec. 14, 2022. Walters Gardens, Inc. obtained the new plant and information about the new plant directly from the inventor. No plants of *Stokesia* 'Riptide' have been sold or offered for sale in this country or anywhere in the world nor has any disclosure of the new plant been made more than one year prior to the filing date of this application, and such sale or disclosure within one year was either derived directly or indirectly from the inventor.

BACKGROUND AND ORIGIN OF THE PLANT

The present invention relates to the new and distinct plant, *Stokesia laevis* 'Riptide', hereinafter also referred to as 'Riptide', and the new plant as a new and unique selection of Stokes' Aster. The new plant is useful in the ornamental landscape as an accent, en masse, or in a container.

'Riptide' was hybridized under the direction of a professor at North Carolina State University prior to the summer of 2011 and sown at a wholesale perennial nursery in Zeeland, Michigan in late winter of 2018. The new plant was selected by the inventor as a single seedling from a cross made between a proprietary seedling with maroon flowers assigned the name 'Maroon' (not patented) as the female parent and 'Peachie's Pick' as the male parent at a . wholesale perennial nursery in Zeeland, Michigan. The new plant was originally selected as growing in full-sun trials in the summer of 2019 at a wholesale perennial nursery in Zeeland, Michigan. While in the trials, the new plant was assigned the breeder code 18-29-1. Asexual propagation of the new variety by division since in the fall of 2019 at the same nursery and later by sterile shoot tip tissue culture has demonstrated that the new plant maintains its unique characteristics and is capable of reproducing identical individuals in successive generations.

SUMMARY OF THE INVENTION

'Riptide' differs from all other Stoke's Aster known to the applicant. The nearest known cultivars are: 'Purple Parasols' U.S. Plant Pat. No. 10,660, 'Colorwheel' U.S. Plant Pat. No. 12,718, 'Purple Pixie' U.S. Plant Pat. No. 19,833, 'Mels Blue' U.S. Plant Pat. No. 23,090, 'Synstokhar' U.S. Plant Pat. No. 28,305, 'Blue Danube' (not patented), 'Klaus Jelitto' (not patented), 'Mini Mels' U.S. Plant Pat. No. 32,136, and 'Mega Mels' U.S. Plant Pat. No. 32,107.

'Purple Parasols' has a smaller habit and the flowers are a slightly different color. 'Colorwheel' has a taller habit, flowers that open white and progress to a light lavender and finally deep purple. 'Purple Pixie' has a much shorter habit with flowers that are more violet-blue. 'Mels Blue' is slightly taller with flowers of violet-blue to violet. 'Synstokhar' has a much shorter habit with light violet flowers. 'Blue Danube' has lavender blue flowers on plants with a slightly shorter habit. 'Klaus Jelitto' has a slightly smaller habit with flowers of medium to powder blue. 'Mini Mels' and 'Mega Mels' both have smaller habits and yellow flower centers with dark purple and light violet ray petals respectively. 'Mini Mels' has much smaller flowers and 'Mega Mels' has larger flowers.

The female parent has burgundy-maroon flowers with a more open habit and fewer flowers. The male parent has flowers that are lavender blue with a slightly smaller habit.

*Stokesia* 'Riptide' has several unique characteristics that have been observed. The combination of these traits makes 'Riptide' distinct from the parent plants and all other Stokes' Aster cultivars known to the inventor.

The following unique characteristics, in combination, distinguish 'Riptide' as a new and distinct variety of Stokes' Aster:

1. Compact rounded habit flowering just above the deep-green foliage;
2. Large composite flowers of periwinkle-blue ray florets and purplish-blue disk florets;
3. Long flowering season with branching on strong upright stems.

BRIEF DESCRIPTION OF THE DRAWINGS

The accompanying color photographic drawings illustrate the distinct characteristics of the new plant to the extent reasonably possible through color reproductions.

DETAILED BOTANICAL DESCRIPTION OF THE INVENTION

Figure 1:
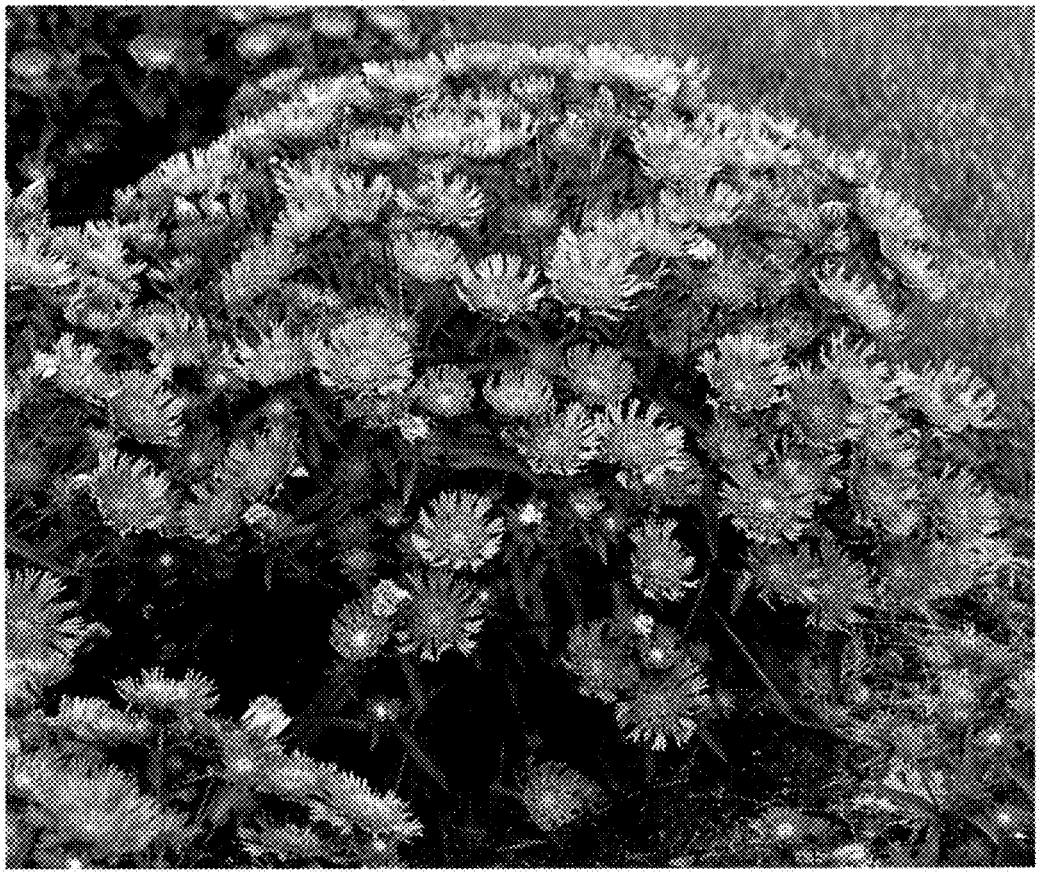
FIG. 1 shows the overall plant in a landscape in full flower.
Figure 2:
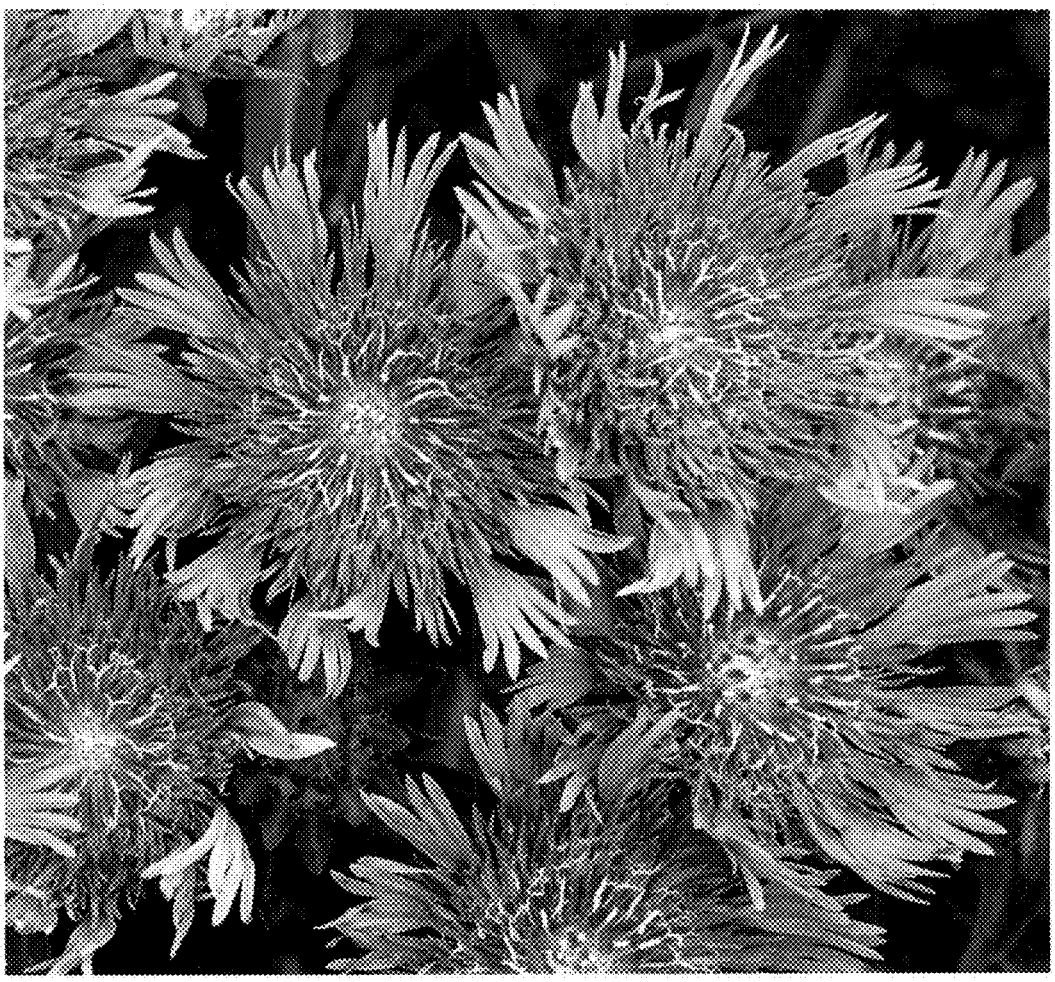
FIG. 2 shows a close-up of some inflorescences from above.

The new plant has not been tested in every possible environmental condition. The phenotype may vary slightly with different growing conditions, such as light intensity, temperature, fertility, and water availability, without, however, any variation in the genotype.

The new plant being described is a two-year-old plant growing in a full-sun display garden in Zeeland, Michigan in sandy loam soil. All color descriptions are based on the 2015 copyright edition of The Royal Horticultural Colour Chart and accompanying designation, except where general dictionary terms are used.

*Plant habit*.—herbaceous perennial, rounded mound with numerous stiffly upright leaves, especially when young; about 25 inflorescence stems per plant.

*Plant size*.—foliage to about 74 cm wide and 37 cm tall; branched inflorescences to about 45 cm tall.

*Root*.—dense, thick, fibrous; color variable depending on soil matrix, typically, between RHS 158D and RHS 164D.

*Stem*.—about 25 per plant; stiff; upright; cylindrical; branched; floccose; to about 45 cm long and 8 mm diameter at base; with typically six cauline leaves; average internode distance about 3.8 cm.

*Stem color*.—

*Parentage*.—female or seed parent is 'Marchoon', male or pollen parent is 'Peachie's Pick'.

*Foliage*.—lanceolate; acute apex; cuneate base; margin entire; glabrous and matte adaxial and abaxial.

*Foliage size*.—to about 22 cm long and 3.6 cm wide.

*Leaf color*.—young adaxial nearest RHS 146B, abaxial between RHS 146B and RHS 146C; mature adaxial nearest RHS 137B, abaxial nearest RHS 147B.

*Veins*.—pinnate; glabrous adaxial and abaxial.

*Vein color*.—adaxial midrib between RHS 146D and RHS 145C, secondary nearest RHS 146C; abaxial midrib between RHS 146D and RHS 145C, secondary veins proximally between RHS 146D and RHS 145C, distally nearest RHS 146C.

*Cauline leaves*.—six; lanceolate; acute apex, partially clasping base; margin entire or with five to eight apiculate teeth about 2 mm long in the basal 10 mm; color same as basal leaves.

*Petiole*.—slightly concavo-convex; glabrous adaxial and abaxial; size to about 15 cm long, 10 mm wide at flared base and 7 mm wide below blade.

*Petiole color*.—adaxial center nearest RHS 145D, distal margin nearest RHS 137B, base blushed lightly with nearest RHS 59C; abaxial center nearest RHS 145C, distal margin nearest RHS 146B, base blushed lightly with nearest RHS 59C.

*Inflorescence*.—capitulum; four to eight per stem; with about 20 to 24 ray florets and about 120 to 150 disk florets; 10 cm wide and 4 cm tall.

*Peduncle*.—branched, erect, corymb, branches 3 to 15 cm long on stems to 45 cm tall, 2 to 3 mm diameter at the base; 25 per plant with initial flowering, to 60 per plant per season.

*Peduncle color*.—proximally between RHS 146D and RHS 145A, distally where exposed to heavy light between RHS 187B and RHS 144A, hair nearest RHS 202D.

*Flower period*.—-early summer through late summer or fall if deadheaded.

*Inflorescences per plant*.—140 to 175 during the main period, 250 to 400 per season.

*Lasting*.—about 2 weeks on plant, 1.5 weeks as cut.

*Inflorescence bud size*.—2 to 3 cm diameter, 1.5 to 3.5 cm tall.

*Inflorescence bud color*.—exposed petals three to five days before petals are horizontal nearest RHS 85B.

*Ray florets*.—20 to 24 per flower; sterile; with single whorl around the exterior of inflorescence; ligule distally deeply cleft into about 5 lobes, rarely 7 lobes, with acute apices; basal 17 mm tubular; to 48 mm long, to 16 mm wide at apex, 3 to 5 mm wide at the base, lobes 10 to 16 mm long and 2 mm to 3 mm wide.

*Ray floret color*.—when first horizontal adaxial distal and middle portion nearest RHS N88C, inner corolla tube nearest RHS NN155B, when first horizontal abaxial distal portion nearest RHS N84C, center portion between RHS N87A and RHS N87B, basal portion nearest RHS NN155C; when mature adaxial distal lobes and middle portion nearest RHS 90D and proximal corolla tube nearest RHS NN155C and distal corolla tube nearest RHS 83C; when mature abaxial distal and middle portion between RHS 85B and RHS 85A, distal corolla tube nearest RHS 83D and basal corolla tube portion between RHS 84A and RHS NN155D.

*Disc florets*.—120 to 150 per inflorescence; perfect; corolla to 27 mm long, 6 mm wide at the apex with up to 4 deeply cleft lobes; lobes to 10 mm long and 2 mm to 3 mm wide; base 1 mm diameter.

*Disk corolla color*.—when first opening adaxial and abaxial between RHS N82B and RHS N82C distally and between RHS N82A and RHS N82B in corolla tube; in mid- and full maturity adaxial and abaxial distal portion between RHS N82D and RHS N82C, corolla tube adaxial and abaxial nearest RHS N82D in middle and distal portion and base nearest RHS NN155C.

*Androecium*.—adnate to inner corolla; connate. Filaments: five; adnate to inner corolla in proximal 11 mm, free in distal 2 mm; to 2 mm long and about 0.2 mm diameter; color proximally nearest RHS 85D where adnate, free portion nearest RHS NN155C. Anther: connate, fully surrounding style; 3 mm long and fused to about 0.7 mm diameter; color nearest RHS NN155B. Pollen: abundant; color nearest RHS NN155B.

*Gynoecium*.—120 to 150 per flower. Style: straight; to 18 mm long and 0.2 mm diameter; color nearest RHS NN155C Stigma: bifid; reflexed 180°; to about 4 mm long and 0.2 mm diameter; color nearest RHS NN155B. Ovary: about 1 mm long; color nearest RHS 155C.

*Involucre*.—arranged in two sets below inflorescence; outer set with about 33 lanceolate phyllaries in three to four whorls, acute apex, truncate base; margin dentate with 9 to 10 teeth with apiculate apices to about 2 mm to 2.5 mm long, to 31 mm long and 9 mm across including teeth decreasing distally, color identical to leaves; inner set with about 37 lanceolate phyllaries in about three whorls, acute and ciliolate apex, truncate base, margin entire, to about 12 mm long and 4 mm across, adaxial and abaxial margin translucent to nearest RHS 155B, adaxial and abaxial nearest RHS 144A next to margin and transitioning to between RHS 145C and RHS 145B in center.

*Seeds*.—about 120 to 150 per flower; angular; to about 3.5 mm long by 1.5 mm wide and near RHS 199A when mature.

Rooted tissue culture plugs finish to flower in 10 to 12 weeks in 3.8-liter containers.

Plant vigor and growth rate are moderate to good.

The plant does not show any pest or disease resistance or susceptibility other than what is normal for *Stokesia*.

I claim:

1. The new and distinct *Stokesia laevis* plant named 'Riptide' as herein described and illustrated.

* * * * *